United States Patent [19]

Duan et al.

[11] Patent Number: 5,389,376
[45] Date of Patent: Feb. 14, 1995

[54] PRESSURE-SENSITIVE POLY(N-VINYL LACTAM) ADHESIVE COMPOSITION AND SKIN COVERING ARTICLES USING SAME

[75] Inventors: Daniel C. Duan, St. Paul, Minn.; Robert A. Asmus, Hudson Township, St. Croix County, Wis.; Timothy M. Dietz; Rosa Uy, both of St. Paul, Minn.; Olester Benson, Jr., Woodbury, Minn.

[73] Assignee: Minnesota Mining and Manufacturing Company, St. Paul, Minn.

[21] Appl. No.: 139,516

[22] Filed: Oct. 15, 1993

Related U.S. Application Data

[62] Division of Ser. No. 792,442, Nov. 15, 1991, Pat. No. 5,276,079.

[51] Int. Cl.$^6$ .............................................. A61F 13/02
[52] U.S. Cl. ..................................... 424/448; 424/449
[58] Field of Search ................................ 424/449, 448

[56] References Cited

U.S. PATENT DOCUMENTS

| | | | |
|---|---|---|---|
| 3,645,835 | 2/1972 | Hodgson | 161/146 |
| 3,900,378 | 8/1975 | Yen et al. | 204/159.14 |
| 4,089,832 | 5/1978 | Yamauchi et al. | 260/29.6 |
| 4,273,135 | 6/1981 | Larimore et al. | 128/640 |
| 4,310,509 | 1/1982 | Berglund et al. | 424/28 |
| 4,352,359 | 10/1982 | Larimore et al. | 128/640 |
| 4,524,087 | 6/1985 | Engel | 427/2 |
| 4,539,996 | 9/1985 | Engel | 128/640 |
| 4,554,924 | 11/1985 | Engel | 128/640 |
| 4,595,001 | 6/1986 | Potter et al. | 128/156 |
| 4,646,730 | 3/1987 | Schonfeld et al. | 728/156 |
| 4,699,146 | 10/1987 | Sieverding | 128/640 |
| 4,715,382 | 12/1987 | Strand | 128/640 |
| 4,750,482 | 6/1988 | Sieverding | 128/156 |
| 4,771,783 | 9/1988 | Roberts | 128/640 |
| 4,792,400 | 12/1988 | Dougherty et al. | 210/500.1 |
| 4,795,516 | 1/1989 | Strand | 156/235 |
| 4,798,642 | 1/1989 | Craighead et al. | 156/252 |
| 4,846,185 | 7/1989 | Carim | 128/641 |
| 4,848,353 | 7/1989 | Engel | 128/640 |
| 4,849,224 | 7/1989 | Chang et al. | 424/434 |
| 4,855,294 | 8/1989 | Patel et al. | 514/212 |
| 4,904,247 | 2/1990 | Therriault et al. | 604/304 |
| 4,931,282 | 6/1990 | Asmus et al. | 424/448 |
| 4,989,607 | 2/1991 | Keusch et al. | 128/640 |
| 5,012,810 | 5/1991 | Strand et al. | 128/640 |

FOREIGN PATENT DOCUMENTS

| | | |
|---|---|---|
| 0107376 | 5/1984 | European Pat. Off. . |
| 0184470 | 11/1986 | European Pat. Off. ...... A61L 15/06 |
| 0322098 | 6/1989 | European Pat. Off. . |
| WO89/07951 | 9/1989 | WIPO . |

OTHER PUBLICATIONS

Errede, "Molecular Interpretations of Sorption in Polymers Part I", *Advances in Polymer Science*, vol. 99, Springer-Verlag, Berlin Heidelberg Germany (pp. 22–36, 1991).

Rosiak et al., "Hydrogel Dressings HDR", American Chemical Society Abstract, Aug. 1990 Meeting.

Rosiak et al., "Fast Reaction of Irradiated Polymers–I. Crosslinking and Degradation of Polyvinylpyrrolidone", Radiat. Phys. and Chem. vol. 36, 6, pp. 747–755, 1990.

Linke et al., "PVP-A Versatile Specialty Polymer", *Polymer News*, vol. 12, pp. 232–237, 1987.

*Primary Examiner*—D. Gabrielle Phelan
*Attorney, Agent, or Firm*—Gary L. Griswold; Walter N. Kirn; John H. Hornickel

[57] ABSTRACT

A hydrophilic, pressure-sensitive adhesive composition prepared by irradiating solid poly(N-vinyl lactam) with ionizing radiation to crosslink the poly(N-vinyl lactam) and thereafter mixing the radiation-crosslinked poly(N-vinyl lactam) with essentially unirradiated plasticizer in an amount sufficient to form a cohesive, pressure-sensitive adhesive composition. The composition is useful as a biomedical adhesive for transmitting or receiving electrical signals as a component of a biomedical electrode. The composition is also useful as a drug delivery device to deliver pharmaceuticals or other active ingredients to or through mammalian skin. The composition is also useful as a component in a skin covering for protecting mammalian skin or mammalian skin openings with antimicrobial agents. A method of preparation of the composition is also disclosed.

28 Claims, 2 Drawing Sheets

PRESSURE-SENSITIVE POLY(N-VINYL LACTAM) ADHESIVE COMPOSITION AND SKIN COVERING ARTICLES USING SAME

This is a division of application No. 07/792,442 filed Nov. 15, 1991, now U.S. Pat. No. 5,276,079.

FIELD OF THE INVENTION

This invention relates to a hydrophilic pressure-sensitive adhesive composition formed from the mixture of a solid, radiation-crosslinked poly(N-vinyl lactam) and an essentially unirradiated plasticizer. This invention also relates to a method for producing the composition by radiation-crosslinking solid poly(N-vinyl lactam) and mixing the radiation-crosslinked poly(N-vinyl lactam) with a plasticizer to render a cohesive, swellable, and pressure-sensitive adhesive composition.

BACKGROUND OF THE INVENTION

Many medical adhesives are known. Often, these adhesives are copolymers of hydrophobic water-insoluble monomers such as isooctyl acrylate and a small amount of a water-soluble monomer such as a short chain $\alpha, \beta$-unsaturated carboxylic acid or an N-vinyl lactam. While these copolymers make excellent medical adhesives, the presence of substantial amounts of ionic or highly polar solvents results in phase separation.

Conductive adhesives have been known for many years. One class of conductive adhesives has employed homopolymers or copolymers of N-vinyl lactams such as N-vinyl-2-pyrrolidone. U.S. Pat. Nos. 4,273,135 and 4,352,359 (both Larimore et al.) disclose non-ionic water-soluble polymers prepared from N-vinyl lactams. However, no crosslinking of such polymers is disclosed. Crosslinking allows for higher amounts of a plasticizer for the composition without reducing cohesiveness of the composition below acceptable levels.

U.S. Pat. Nos. 4,527,087 and 4,539,996 (both Engel) disclose the polymerization of an unsaturated free-radically polymerizable material which is soluble in a polyhydric alcohol, where the unsaturated material is crosslinked with a multifunctional unsaturated free-radically polymerizable material. U.S. Pat. No. 4,554,924 (Engel) discloses a conductive adhesive formed by an essentially solventless free-radical polymerization of an adhesive precursor, having a polyhydric alcohol, at least one non-ionic monomer, an initiator, a crosslinker, and an ionizable salt present in amounts sufficient to render the composition electrically conductive. One of the non-ionic free-radically polymerizable monomers can be N-vinyl pyrrolidone. The essentially solventless precursor can be coated onto the electrode plate or transfer sheet and exposed to either heat or actinic radiation which forms the electrically conductive pressure-sensitive adhesive. The precursor may also be exposed to electron beam radiation to facilitate the crosslinking.

U.S. Pat. No. 4,848,353 (Engel) discloses an electrically-conductive, pressure-sensitive adhesive composition of a homogeneous mixture of a copolymer matrix and a plasticizing, electrically-conductive solution. The composition need not be covalently crosslinked but a crosslinker may be used. The copolymer matrix is formed from a free-radical polymerizable adhesive precursor having at least one water-soluble hydrogen bond donating monomer, at least one water-soluble hydrogen bond accepting monomer, and either a photo or thermal free radical initiator. N-vinyl lactams may be used as the hydrogen bond accepting monomer with N-vinyl pyrrolidone being preferred.

European Pat. Publication 0322098 (Duan) discloses a crosslinked hydrophilic polymer composition which is useful as a pressure-sensitive adhesive. The composition comprises a crosslinked, cohesive, swellable polymeric matrix and a plasticizing solution. The crosslinked, cohesive, swellable polymeric matrix is formed from the free-radical polymerization of a precursor having a monomeric species of N-vinyl lactam, and a crosslinker of a multi-ethylenicaliy unsaturated compound wherein the ethylenic groups are vinyl, allyl, or methallyl groups bonded to nitrogen or oxygen atoms. The crosslinker and plasticizer are present in controlled amounts sufficient to render a pressure-sensitive adhesive swellable matrix.

A continuing concern for the preparation of hydrophilic polymers used as medical adhesives is biocompatibility. Not only must the pressure-sensitive adhesive composition adhere to mammalian skin, but also the adherence to mammalian skin must not cause skin irritation, toxicity reaction, or other deleterious effects of contacting a polymeric composition to living tissue. Compositions which are prepared by the polymerization of monomers must proceed through exacting procedures to minimize the residual presence of unreacted monomers. When crosslinking agents are employed to chemically crosslink a polymer, such crosslinking agents can also leave residuals and produce undesired byproducts.

Another approach to preparing conductive adhesives involves irradiation crosslinking of uncrosslinked polymers in the presence of plasticizers. U.S. Pat. Nos. 4,699,146 and 4,750,482 (Sieverding) disclose a water-insoluble, hydrophilic elastomeric, pressure-sensitive adhesive that includes at least one irradiation crosslinked synthetic organic polymer and an adhesive plasticizer. The crosslinked polymer is formed by dispersing or solubilizing at least one suitable gel-forming, uncrosslinked synthetic organic polymer in a plasticizer that has a composition the same as or different than the adhesive plasticizer, and then subjecting the resulting solution or dispersion to an appropriate dosage of irradiation. One example of an uncrosslinked synthetic organic polymer includes repeating units derived from an N-vinyl lactam monomer which is preferred among monomeric candidates. The solubilizing plasticizer includes at least one substantially non-volatile elasticizer and conveniently includes a volatile solvent which can be aqueous, nonaqueous, or a mixture. Preferably the volatile solvent is water. The substantially non-volatile elasticizer can be a polyhydric alcohol, a lactam, a glycol, among others listed. But it is necessary that the elasticizer present during the irradiation treatment step be irradiation crosslinking compatible. Glycerin tends to reduce effectiveness of irradiation crosslinking and should not be present prior to irradiation treatment in an amount greater than about 5% of the total formula weight. Glycerin can be added once crosslinking has been completed.

However, ionizing radiation of a plasticizing liquid can produce small molecule contaminants and other byproducts when ionizing crosslinking is performed on polymers in the presence of other materials. Further, adhesive gels containing levels of plasticizing glycerin greater than about 5% of the total formula weight cannot be directly prepared since glycerin containing precursor solutions do not crosslink upon exposure to ionizing radiation. Thus, these Sieverding patents teach a cumbersome process of plasticizing an ionizing radiation crosslinked polymer.

Other U.S. patents have also disclosed the irradiation of poly(N-vinyl lactam) in the presence of other materials. U.S. Pat. No. 4,089,832 (Yamauchi et al.) discloses the crosslinking of polyvinyl pyrrolidone while in aqueous solution followed by pulverizing the crosslinked product and mixing with a plastic substance selected from thermoplastic or thermohardenable plastics.

U.S. Pat. No. 3,900,378 (Yen et al.) discloses a particulate polymer useful as a soil amendment prepared by blending a mixture of a hydrophilic polymer, a pulverulent inert filler, and water prior to exposing the mixture to ionizing radiation for a period of time to crosslink the polymer.

U.S. Pat. No. 4,646,730 (Schonfeld et al.) discloses an aqueous dispersion of polyvinyl pyrrolidone, silver sulfadiazine, magnesium trisilicate and water, followed by exposure to E-Beam radiation to provide a hydrogel product having a uniform deep yellow color retained over a long shelf life.

U.S. Pat. No. 4,989,607 (Keusch et al.) discloses hydrophilic gels which are nonstringy and highly conductive, prepared from an aqueous mixture of poly(vinylpyrrolidone) a viscosity-enhancing hydrophilic polymer, and an electrolyte to provide a uniform cohesive aqueous mixture substantially free of unbound water. The aqueous mixture is applied or cast to a desired thickness and subjected to crosslinking high energy irradiationto initiate or precipitate the crosslinking polymer chains.

European Pat. Publication 0 107 376 (Thompson et al.) discloses a gel dressing made from poly(vinylpyrrolidone) having a high molecular weight by dissolving the polymer in water and crosslinking the polymer with ionizing radiation for time sufficient to change the viscosity of the solution.

U.S. Pat. No. 4,792,400 (Dougherty et al.) discloses preparation of a particulate, normally solid, water-insoluble vinyl lactam polymer containing between about 0.5 and about 10% of non-crosslinked and/or unsaturated sites on the high molecular weight polymer chains. These polymers have an average particle size sufficient to be retained on a filtering means. The water-insoluble polymer is subjected to irradiation with radiant energy at a dosage level of between about 0.001 and about 20 megarads. The polymeric materials can be irradiated in a dry state or as a liquid slurry.

U.S. Pat. No. 4,904,247 (Therriault et al.) discloses a pressure-sensitive hydrophilic laminate composite comprising layers of a tacky pressure-sensitive adhesive hydrophilic polymer blend and a non-tacky hydrophilic polymer blend. The blends are preferably comprised of homopolymers or copolymers of N-vinyl lactam, a relatively hydrophobic water-insoluble acrylate polymer and water soluble plasticizer. The blends have a microphase separated morphology. Pressure-sensitive adhesiveness is determined by the amount of N-vinyl lactam polymer and the amount of plasticizer in the blend.

SUMMARY OF THE INVENTION

Unexpectedly, superior hydrophilic, medically useful, pressure-sensitive adhesive compositions are prepared by a process which both avoids residual monomers and by-products of chemical crosslinking and also avoids by-products of irradiated plasticizer and other additives.

A hydrophilic, pressure-sensitive adhesive composition of the present invention comprises a solid, radiation-crosslinked poly(N-vinyl lactam) and an essentially unirradiated plasticizer present in an amount sufficient to form a cohesive, pressure-sensitive adhesive composition.

A hydrophilic, pressure-sensitive adhesive composition of the present invention can be prepared by a method comprising (a) irradiating solid non-crosslinked poly(N-vinyl lactam) with ionizing radiation to crosslink the poly(N-vinyl lactam) and (b) mixing the radiation-crosslinked poly(N-vinyl lactam) with an essentially unirradiated plasticizer in an amount sufficient for the composition to be a cohesive, pressure-sensitive adhesive.

"Solid" means that poly(vinyl lactam) is not required to be mixed with any other material prior to irradiation to crosslink such poly(vinyl lactam). No mixing with solvents, plasticizers or chemical crosslinking agents is required to prepare radiation-crosslinked poly(vinyl lactam) useful for the present invention. Commercially available non-crosslinked poly(vinyl lactam) can be employed in particulate form for irradiation to crosslink such poly(vinyl lactam).

"Essentially unirradiated" means that plasticizer useful with solid, radiation-crosslinked poly(N-vinyl lactam) is neither subjected to any irradiation during the crosslinking of such solid poly(N-vinyl lactam) nor is subjected to any irradiation at any other time at a dosage which would degrade the plasticizer.

A hydrophilic, pressure-sensitive adhesive composition of the present invention can be used as a conductive adhesive component of a biomedical electrode, as a mammalian skin-contacting adhesive layer in a medical tape, or as an adhesive in a mammalian skin pharmaceutical delivery device.

It is a feature of the invention that it is possible to prepare hydrophilic pressure-sensitive adhesive compositions by subjecting poly(N-vinyl lactam) existing in a solid form to crosslinking with ionizing radiation.

It is another feature of the invention that any plasticizer needed to render radiation-crosslinked poly(N-vinyl lactam) a cohesive, pressure-sensitive adhesive can be added after the poly(N-vinyl lactam) has been radiation-crosslinked.

It is another feature of the invention that biocompatible and/or therapeutic and/or ionically-unirradiated plasticizer or to the plasticized composition, eliminating the possibility of exposure of the biocompatible and/or therapeutic and/or ionically-conductive materials to deleterious effects of ionizing radiation otherwise administered in dosages sufficient to crosslink the hydrophilic polymer.

It is another feature of the present invention that biocompatible and/or therapeutic and/or ionically-conductive materials added to the pressure-sensitive adhesive composition facilitate use as biomedical electrodes, pharmaceutical delivery devices, or mammalian skin coverings.

It is an advantage of the invention that the pressure-sensitive adhesive compositions prepared by processes of the present invention minimize the presence of radiation-degraded plasticizer, radiation-degraded biocompatible and/or therapeutic and/or ionically-conductive materials, residual monomers or crosslinking agents, or other byproducts of reaction or crosslinking of a polymer in the presence of other materials.

It is another advantage of the invention that plasticizing of radiation-crosslinked poly(N-vinyl lactam) can include glycerin added after radiation-crosslinking has been completed.

Discussion of embodiments of the invention follows.

EMBODIMENTS OF THE INVENTION

Hydrophilic, Pressure-Sensitive Adhesive Composition

A hydrophilic, pressure-sensitive adhesive composition of the present invention comprises a swellable, poly(N-vinyl lactam) radiation-crosslinked while in a solid form and an essentially unirradiated plasticizer present in an amount sufficient to form a cohesive, pressure-sensitive adhesive composition. The amount of plasticizer to be mixed with the radiation-crosslinked swellable poly(N-vinyl lactam) can range from about 50 to about 90 weight percent of the composition. Consequently, exclusive of any biocompatible and/or therapeutic and/or ionically-conductive materials to be added to the composition, the weight percent of the solid, radiation-crosslinked, swellable poly(N-vinyl lactam) can be from about 10 to about 50 weight percent. When the poly(N-vinyl lactam) is poly(N-vinyl pyrrolidone), the weight percent of poly(N-vinyl pyrrolidone) can range from about 15 to about 45 percent and preferably from about 20 percent to about 40 percent.

Poly(N-vinyl lactam) in a Solid Form

Poly(N-vinyl lactam) useful in the present invention can be in any form of solid susceptible to being radiation-crosslinked. Nonlimiting examples of solid forms include particles, pellets, sheets, flakes, and bulk objects of various shapes, and coated objects of various shapes. Preferably, poly(N-vinyl lactam) is in the form of particles of a size less than about 1 cm, desirably from about 0.1 $\mu$m to 250 $\mu$m and preferably from about 10 $\mu$m to about 75 $\mu$m.

Poly(N-vinyllactam) in a solid form can be a noncrosslinked homopolymer or a noncrosslinked copolymer containing N-vinyl lactam monomeric units, which after irradiation is swellable in a plasticizer biocompatible with mammalian skin. Preferably, noncrosslinked homopolymer or noncrosslinked copolymer is soluble in plasticizer biocompatible with mammalian skin in the absence of radiation crosslinking. N-vinyl lactam monomeric units comprise a majority of total monomeric units of the polymer.

Nonlimiting examples of N-vinyl lactam monomers are N-vinyl-2-pyrrolidone; N-vinyl-2-valerolactam; N-vinyl-2-caprolactam; and mixtures of any of the foregoing. Preferably, the N-vinyl lactam is N-vinyl-2-pyrrolidone. Preferably, the poly(N-vinyl lactam) is a homopolymer of N-vinyl-2-pyrrolidone.

Nonlimiting examples of non-N-vinyl lactam comonomers useful with N-vinyl lactam monomeric units include N,N-dimethylacrylamide, acrylic acid, methacrylic acid, hydroxyethylmethacrylate, acrylamide, 2-acrylamido-2-methyl-1-propane sulfonic acid or its salt, and vinyl acetate.

The N-vinyl lactam monomeric units comprise no less than about 50 weight percent of the monomeric units present in the poly(N-vinyl lactam) in solid state form. More preferably, the N-vinyl lactam monomeric units comprise 70 to 100 percent by weight of the poly(N-vinyl lactam) and most preferably 90 to 100 percent by weight of the poly(N-vinyl lactam).

Noncrosslinked N-vinyl lactam homopolymer and N-vinyl pyrrolidone/vinyl acetate copolymers are commercially available. Nonlimiting sources of commercially available poly(N-vinyl pyrrolidone) useful for the present invention include Aldrich Chemical Co. of Milwaukee, Wisc., BASF of Parsippany, N.J., ISP (GAF) of Wayne, N.J., Dan River Corporation of Danville, Va., and Spectrum Chemical Manufacturing Corporation of Gardena, Calif.

Poly(N-vinyl lactam) can have a Fikentscher K-value of at least K-15 and preferably at least K-60, and most preferably at least K-90. Fikentscher K-values are described in Molyneaux, Water-Soluble Polymers: Properties and Behavior, Vol. 1, CRC Press, 1983, pp. 151–152.

After exposure to ionizing radiation, poly(N-vinyl lactam) can have a Swelling Capacity of at least about 15 in water, preferably at least about 30 in water, and most preferably at least about 40 in water. Swelling Capacity, S, is a measurement of the milliliters of water sorbed per gram of solid, radiation-crosslinked poly(N-vinyl lactam), approximated by equation I:

$$S = \frac{\left[(PVP\text{ WT.} + H_2O\text{ WT.}) \times \frac{\text{GEL HEIGHT}}{\text{TOTAL HEIGHT}}\right] - PVP\text{ WT.}}{PVP\text{ WT.}} \quad \text{I}$$

where PVP wt. is polymer composition weight, $H_2O$ wt. is water weight, Gel Height is height of swollen PVP in a vial, and Total Height is total height of material in the vial.

Swelling Capacity correlates to a measurement of polymer swelling as a function of chemical crosslinking units in poly(N-vinyl lactam), according to the equation II:

$$S = C(\lambda^{\frac{1}{2}} - \lambda_o^{\frac{1}{2}}) \quad \text{II}$$

where S is a measurement of water sorbed per gram of polymer, C is a constant characteristic of the polymer, i.e., the volume of water sorbed per gram of polymer, $\lambda$ is the average number of backbone carbon atoms in the polymer segments between crosslinked junctions, and $\lambda_o$ is the average number of backbone carbon atoms between Crosslinked junctions when S is zero. Swelling capacity and this equation are discussed in Errede, "Molecular Interpretations of Sorption in Polymers Part I" *Advances in Polymer Science* Vol 99, Springer-Verlag, Berlin Heidelberg Germany (pp. 21–36, 1991), the disclosure of which is incorporated by reference.

Plasticizer

Hydrophilic, pressure-sensitive adhesive compositions of the present invention contain a plasticizer for the solid, radiation-crosslinked poly(N-vinyl lactam). The plasticizer can be any plasticizer which can swell solid, radiation-crosslinked poly(N-vinyl lactam) and which is biocompatible with mammalian skin.

Nonlimiting examples of plasticizers useful to swell the poly(N-vinyl lactam) include monohydric alcohols (e.g., ethanol and isopropanol), polyhydric alcohols, (e.g., ethylene glycol, propylene glycol, polyethylene glycol (Molecular Weight between 200 and 600) and glycerin), ether alcohols (e.g., glycol ethers), other polyol plasticizers which do not cause mammalian skin irritation or toxic reaction, and water.

Depending on the ultimate use desired for the hydrophilic pressure-sensitive adhesive composition, a mixture of a essentially non-volatile plasticizer and a volatile plasticizer can be used, such as a mixture of non-volatile plasticizer, (e.g., glycerin or polyethylene glycol) with water. Alternatively, only a non-volatile plasticizer such as glycerin or polyethylene glycol, or only a volatile plasticizer such as water, can be used to render a cohesive, pressure-sensitive adhesive composition.

For this invention, "essentially non-volatile" means that a plasticizer as used in the present invention will render solid, radiation-crosslinked poly(N-vinyl lactam) sufficiently cohesive and pressure-sensitive adhesive, such that less than ten percent (10%) of a given volume of plasticizer evaporates after exposure to processing conditions or to storage conditions.

The plasticizer can be added in an amount ranging from about 50 to about 90 weight percent of the adhesive composition and preferably from about 60 to about 80 weight percent. Of essentially non-volatile plasticizers, glycerin and polyethylene glycol are preferred, with polyethylene glycol most preferred. Glycerin can comprise up to 100 weight percent of the plasticizer. Polyethylene glycol can comprise up to 100 weight percent of the plasticizer. Polyethylene glycol of either 300 molecular weight or 400 molecular weight is preferred with 300 molecular weight more preferred.

When the adhesive compositions are used as an electrically conductive component of biomedical electrodes, the plasticizer can also optionally include water to improve ionic conductivity in the composition and can include either glycerin or polyethylene glycol. In this instance, water is used as a plasticizer comprising from about 20 percent to about 100 percent and preferably at least about 30 percent by weight of the plasticizer used.

Biocompatible and/or Therapeutic and/or Ionically-Conductive Additives

Depending upon the use of the hydrophilic, pressure-sensitive adhesive composition of the present invention, various biocompatible and/or therapeutic and/or ionically-conductive materials can be included in the composition.

For example, compositions of the present invention can be used as conductive adhesive in a biomedical electrode with the addition of an ionically-conductive electrolyte to the composition after radiation-crosslinking of the solid poly(N-vinyl lactam) with ionizing radiation without deleteriously affecting the electrolyte or the resulting composition. Nonlimiting examples of electrolyte include ionic salts dissolved in the composition to provide ionic conductivity and can include lithium chloride, lithium perchlorate, sodium citrate, and preferably potassium chloride. Alternatively, a redox couple such as a mixture of ferric and ferrous salts such as sulfates and gluconates can be added.

The amounts of these ionic salts present in compositions of the present invention are relatively small, from about 0.5 to 5 percent by weight of the composition, and preferably about 2 to 3 weight percent. When a redox couple is used in compositions of the present invention, the biomedical electrode can recover from an overload potential. U.S. Pat. No. 4,846,185 (Carim) discloses a redox couple totalling not more than about 20 percent by weight of the adhesive composition.

Hydrophilic, pressure-sensitive adhesive compositions of the present invention can also be used in the delivery of pharmaceuticals to or through mammalian skin, such as topical or transdermal drug delivery systems. The pharmaceutical or other active ingredient can be compounded with the adhesive composition after poly(N-vinyl lactam) has been radiation-crosslinked, minimizing any possible deleterious interaction of the pharmaceutical or active ingredient with ionizing radiation in dosages sufficient to crosslink poly(N-vinyl lactam).

A type of therapeutic procedure both involving application of electrical current to skin of a patient and a pharmaceutical is liontophoresis, which delivers an iontophoretically active pharmaceutical to or through mammalian skin with aid of an electrical current.

The hydrophilic, pressure-sensitive adhesive composition can also be used in therapeutic mammalian skin coverings, such as dressings, wound closure materials, tapes, and the like. Preferably, for mammalian skin covering uses, other biologically active materials can be added to the composition of the present invention after irradiation of poly(N-vinyl lactam) without deleteriously affecting the biologically active material. Nonlimiting examples of such other biologically active materials include broad spectrum antimicrobial agents where it is desired to reduce bacteria levels to minimize infection risk or treat the effects of infections at the skin or skin openings of a mammalian patient. Broad spectrum antimicrobial agents are disclosed in U.S. Pat. No. 4,310,509, which disclosure is incorporated by reference. Nonlimiting examples of other antimicrobial agents include parachlorometaxylenol; triclosan; chlorhexidine and its salts such as chlorhexidine acetate and chlorhexidine gluconate; iodine; iodophors; poly-N-vinyl pyrrolidone-iodophors; silver oxide, silver and its salts, antibiotics (e.g., neomycin, bacitracin, and polymyxin B). Antimicrobial agents can be included in the composition after radiation of poly(N-vinyl lactam) in a weight from about 0.01 percent to about 10 percent by weight of the total composition.

Other biocompatible and/or therapeutic materials can be added to the composition such as compounds to buffer the pH of the composition to provide a non-irritating pH for use with sensitive mammalian skin tissue or to otherwise maximize antimicrobial activity. Also, penetration enhancing agents or excipients can be added to the composition when the pharmaceutical or other active agent for topical or transdermal delivery so requires.

Irradiation Crosslinking of Poly(N-Vinyl Lactam)

Poly(N-vinyl lactam) in any solid form is subjected to ionizing radiation from a high-energy source. Nonlimiting examples of ionizing radiation include alpha, beta, gamma, electron-beam, and x-ray radiation. Of these sources of ionizing radiation, electron-beam irradiation and gamma irradiation are preferred. Sources of electron-beam radiation are commercially available, including an Energy Sciences Inc. Model CB-150 Electrocurtain Electron Beam Processor. Sources of gamma irradiation are commercially available from Atomic Energy of Canada, Inc. using a cobalt-60 high-energy source.

Ionizing radiation dosages are measured in megarads (mRad) or kilograys (kGy). Doses of ionizing radiation can be administered in a single dose of the desired level of ionizing radiation or in multiple doses which accumulate to the desired level of ionizing radiation. The dosage of ionizing radiation cumulatively can range from about 25 kGys to about 400 kGys and preferably from about 25 kGys to about 200 kGys. Preferably, ionizing radiation can achieve the desired level of crosslinking of poly(N-vinyl lactam) when the cumulative dosage of ionizing radiation exceeds 100 kGys (10 mRads).

Poly(N-vinyl lactam) can be irradiated in a solid form with ionizing radiation in a package or container where the temperature, atmosphere, and other reaction parameters can be controlled.

Temperature can range from about $-80°$ C. to about $100°$ C. and preferably from about $10°$ C. to about $35°$ C.

The atmosphere can be air or preferably an inert atmosphere such as nitrogen.

The line speed for electron-beam irradiation can be about 15 meters/minute.

The pressure in the container can be atmospheric, elevated or depressed. Preferably it is atmospheric.

Depending upon the control of the irradiation conditions, poly(N-vinyl lactam) can be irradiated in a batch or continuous process.

Method of Preparing Hydrophilic, Pressure-Sensitive Adhesive Compositions

A method of preparing a hydrophilic, pressure-sensitive adhesive composition of the present invention can employ a minimum number of ecologically compatible manufacturing steps. The solid, radiation-crosslinked poly(N-vinyl lactam) is mixed with essentially unirradiated plasticizer and any other optional additives into a solvent which is essentially volatile at or above ambient temperatures, such as water, ethanol, methanol, and isopropanol. A quantity of the suspension of radiation-crosslinked poly(N-vinyl lactam), essentially unirradiated plasticizer, and any optional additives in the volatile solvent is then cast onto a surface of a substrate, which can be an inert substrate such as a liner for storage before further processing or a surface designed for ultimate use, such as a means for electrical communication having an electrically conductive surface for use as a biomedical electrode. Then the volatile solvent is essentially evaporated by the application of heat, microwave energy, infrared energy, convective air flow or the like, in order to form a cohesive, pressure-sensitive adhesive composition on the substrate. Typically, a drying oven heated to about $65°$ C. can be employed. A product liner can optionally be laminated over the field of pressure-sensitive adhesive composition to protect that field from contamination.

A coating of cohesive, pressure-sensitive adhesive composition can, be applied to a substrate surface. Coating thicknesses can range from about 0.125 mm to about 1.25 mm and preferably from about 0.75 mm to about 1 mm, to yield after evaporation of solvent a coating thickness ranging from about 0.05 mm to about 0.38 mm and preferably from about 0.18 mm to about 0.25 mm. With this extremely thin coating of a conductive and preferably adhesive composition, a low profile and conformable biomedical electrode can be made.

The method can be prepared in a batch process or in a continuous line process. If prepared by a continuous process, the laminate of a liner, field of cohesive, pressure-sensitive adhesive composition, and substrate can be wound on roll for bulk packaging and further processing or can be cut using dies known to those skilled in the art into individual units, such as biomedical electrodes or biomedical electrode subassemblies, for further processing. U.S. Pat. No. 4,795,516 (Strand) and U.S. Pat. No. 4,798,642 (Craighead et al.), which are incorporated by reference herein, disclose processes and equipment useful for a continuous manufacture of biomedical electrodes involving the dispensing of strips of material from rolls and overlaying such strips in a registered continuous manner in order to prepare a strip of electrodes. Further, co-pending, co-assigned U.S. patent application Ser. Nos. 07/686,049 and 07/688,138 disclose methods of preparing biomedical electrode constructions in a continuous strip subassembly.

For example, one method of continuous strip assembly can be the coating of an aqueous mixture of radiation-crosslinked poly(N-vinyl pyrrolidone), polyethylene glycol, and potassium chloride on an electrically conductive surface about 8.9 cm wide, with the coating applied to about the center 5.1 cm section of such width. After evaporation of solvent, the coated electrically conductive surface can be bisected along the strip and also cut orthogonally at about 2.54 cm intervals, yielding a number of electrodes 10 seen in FIG. 1 having dimensions of about 2.54 cm$\times$4.4 cm with a conductive interface portion 18 of 2.54 cm$\times$2.54 cm and a tab portion 20 of 2.54 cm$\times$1.9 cm.

Usefulness of the Invention

Hydrophilic, pressure-sensitive adhesive compositions of the present invention can have many uses as biocompatible medical adhesives such as for receipt or delivery of electrical signals at or through mammalian skin, delivery of pharmaceuticals or active agents to or through mammalian skin, or treatment of mammalian skin or mammalian skin openings against the possibilities of infection.

Biomedical Electrodes

Biomedical electrodes employing hydrophilic, pressure-sensitive adhesive compositions of the present invention having electrolyte contained therein are useful for diagnostic and therapeutic purposes. In its most basic form, a biomedical electrode comprises a conductive medium contacting mammalian skin and a means for electrical communication interacting between the conductive medium and electrical diagnostic, therapeutic, or electrosurgical equipment.

Figure 1:
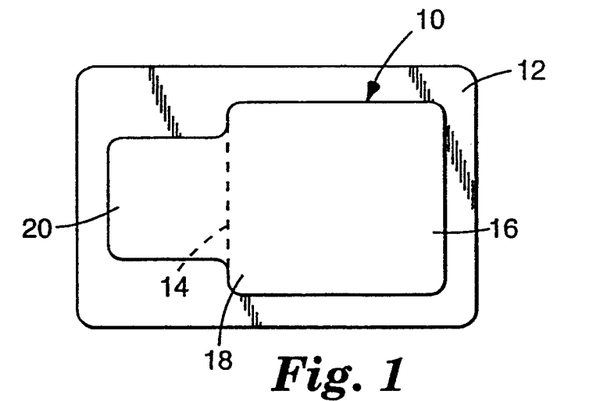
FIG. 1 is a top plan view of a biomedical electrode containing hydrophilic pressure-sensitive adhesive of the present invention.
Figure 2:
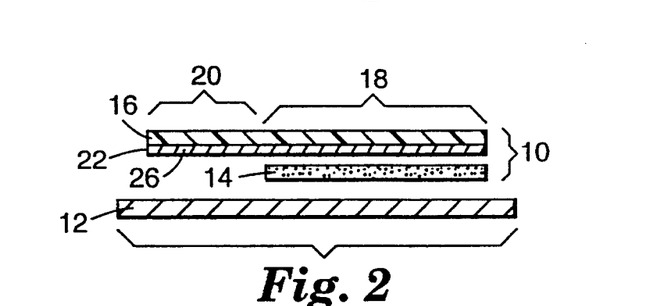
FIG. 2 is an exploded sectional view of the biomedical electrode of FIG. 1.

FIGS. 1 and 2 show either a disposable diagnostic electrocardiogram (ECG) or a transcutaneous electrical nerve stimulation (TENS) electrode 10 on a release liner 12. Electrode 10 includes a field 14 of a biocompatible and adhesive conductive medium for contacting mammalian skin of a patient upon removal of protective release liner 12. Electrode 10 includes means for electrical communication 16 comprising a conductor member having a conductive interface portion 18 contacting field 14 of conductive medium and a tab portion 20 extending beyond, field 14 of conductive medium for mechanical and electrical contact with electrical instrumentation (not shown). Means 16 for electrical communication includes a conductive layer 26 coated on at least the side 22 contacting field 14 of conductive medium.

It is foreseen that a typical ECG conductor member 16 will comprise a strip of material having a thickness of about 0.0.5–0.2 millimeters, such as polyester film and have a coating 26 on side 22 of silver/silver chloride of about 2.5–12 micrometers, and preferably about 5 micrometers thick thereon. Presently preferred is a polyester film commercially available as "Mellinex" 505–300, 329, or 339 film from ICI Americas of Hopewell, Va. coated with a silver/silver chloride ink commercially available as "R-300" ink from Ercon, Inc. of Waltham, Mass. A TENS conductor member 16 can be made of a nonwoven web, such as a web of polyester/cellulose fibers commercially available as "Manniweb" web from Lydall, Inc. of Troy, N.Y. and have a carbon ink layer 26 commercially available as "SS24363" ink from Acheson Colloids Company of Port Huron, Mich. on side 22 thereof. To enhance mechanical contact between an electrode clip (not shown) and conductor member 16, an adhesively-backed polyethylene tape can be applied to tab portion 20 on side 24 opposite side 22 having the conductive coating 26. A surgical tape commercially available from 3M Company as "Blenderm" tape can be employed for this purpose.

Non-limiting examples of biomedical electrodes which can use hydrophilic, pressure-sensitive adhesive compositions of the present invention, either as conductive or non-conductive adhesive fields include electrodes disclosed in U.S. Pat. Nos. 4,527,087; 4,539,996; 4,554,924; 4,848,353 (all Engel); 4,846,185 (Carim); 4,771,713 (Roberts); 4,715,382 (Strand); 5,012,810 (Strand et al.); co-pending and co-assigned U.S. patent application Ser. No. 07/686,049; and co-pending and co-assigned U.S. patent application Ser. No. 07/688,138 the disclosures of which are incorporated by reference herein.

In some instances, the means for electrical communication can be an electrically conductive tab extending from the periphery of the biomedical electrodes such as that seen in U.S. Pat. No. 4,848,353 or can be a conductor member extending through a slit or seam in an insulating backing member, such as that seen in U.S. Pat. No. 5,012,810. Otherwise, the means for electrical communication can be an eyelet or other snaptype connector such as that disclosed in U.S. Pat. No. 4,846,185. Further, the means for electrical communication can be a lead wire such as that seen in U.S. Pat. No. 4,771,783. Regardless of the type of means for electrical communication employed, a hydrophilic, pressure-sensitive adhesive composition of the present invention, containing an electrolyte, can reside as a field of conductive adhesive on a biomedical electrode for diagnostic, therapeutic, or electrosurgical purposes.

Medical Skin Coverings

Medical skin coverings employing hydrophilic, pressure-sensitive adhesive compositions of the present invention, optionally having antimicrobial and other biologically active agents contained therein, are useful for treatment of mammalian skin or mammalian skin openings, preferably against the possibility of infection.

Figure 3:
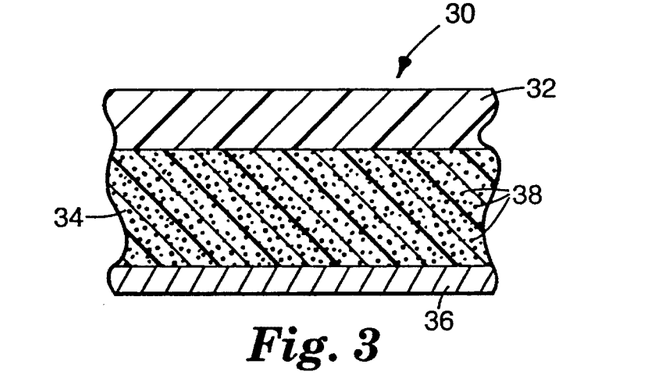
FIG. 3 is a sectional view of a medical mammalian skin covering containing hydrophilic, pressure-sensitive adhesive of the present invention.

FIG. 3 shows a sectional view of a medical skin covering 30 having a backing material 32, a layer 34 of pressure-sensitive adhesive composition of the present invention coated on backing material 32, and protected until use by a release liner 36. Preferably, antimicrobial 38 is contained in layer 34 by adding agent 38 to essentially unirradiated plasticizer or composition prior to coating on backing material 32. Alternatively, layer 34 can be used as a caulkable sealant according to U.S. Pat. No. 4,931,282 (Asmus et al.), the disclosure of which is incorporated by reference herein.

For use, the release liner 36 is removed and the layer 34 of pressure-sensitive adhesive composition can be applied to the skin of the patient as a part of a medical tape, a wound dressing, a bandage of general medicinal utility, or other medical device having water moisture absorbing properties.

The adhesive layer 34 may be coated on a layer of backing material 32 selected from any of several backing materials having a high moisture vapor transmission rate for use as medical tapes, dressings, bandages, and the like. Suitable backing materials include those disclosed in U.S. Pat. Nos. 3,645,835 and 4,595,001, the disclosures of which are incorporated by reference. Other examples of a variety of films commercially available as extrudable polymers include "Hytrel ® 4056" and "Hytrel ® 3548" branded polyester elastomers available from E. I. DuPont de Nemours and Company of Wilmington, Del., "Estane" branded polyurethanes available from B. F. Goodrich of Cleveland, Ohio or "Q-thane" branded polyurethanes available from K.J. Quinn & Co. of Malden, Mass.

The layer 34 of adhesive combined with a layer 32 of suitable backing material can be used as a dressing.

Hydrophilic, pressure-sensitive adhesive compositions of the present invention can be used as discrete gel particles dispersed in a continuous pressure-sensitive adhesive matrix to form a two phase composite useful in medical applications, as described in co-pending, co-assigned U.S. patent application Ser. No. 07/458,246, the disclosure of which is incorporated by reference herein.

The adhesive layer 34 can be coated on the backing layer 32 by a variety of processes, including, direct coating, lamination, and hot lamination. The release liner 36 can thereafter be applied using direct coating, lamination, and hot lamination.

The methods of lamination and hot lamination involve the application of pressure, or heat and pressure, respectively, on the layer of adhesive layer 34 to the backing material layer 32. The temperature for hot lamination ranges from about 50° C. to about 250° C., and the pressures applied to both lamination and hot lamination range from 0.1 Kg/cm$^2$ to about 50 Kg/cm$^2$.

Pharmaceutical Delivery Devices

Pharmaceutical delivery devices employing hydrophilic, pressure-sensitive adhesive compositions of the present invention, optionally having a topical, transdermal, or iontophoretic therapeutic agent and excipients, solvents, or penetration enhancing agents contained therein, are useful for delivery of pharmaceuticals or other active agents to or through mammalian skin.

Figure 4:
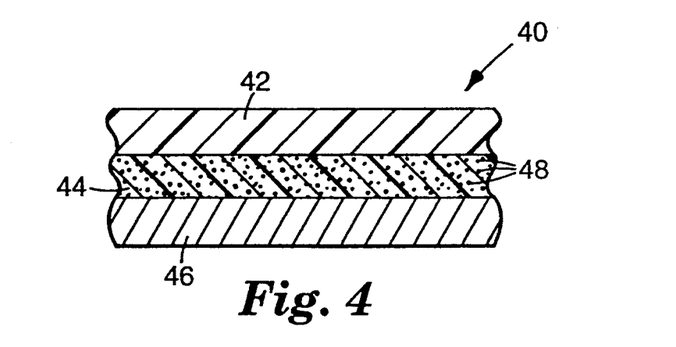
FIG. 4 is a sectional view of a pharmaceutical delivery device containing hydrophilic, pressure-sensitive adhesive of the present invention.

FIG. 4 shows a sectional view of a transdermal or topical drug delivery device 40 having a backing layer 42, a layer 44 containing hydrophilic, pressure-sensitive adhesive composition of the present invention coated thereon and protected by a release liner 46. Other layers can be present between layer 42 and layer 44 to house pharmaceuticals or other therapeutic agents. Otherwise, as shown in FIG. 4, pharmaceutical and other agents 48 are dispersed in adhesive layer 44.

The backing layer 42 can be any backing material known to those skilled in the art and useful for drug delivery devices. Non-limiting examples of such backing materials are polyethylene, ethylene-vinyl acetate copolymer, polyethylene-aluminum-polyethylene composites, and "ScotchPak ™" brand backings commercially available from Minnesota Mining and Manufacturing Company of St. Paul, Minn. (3M).

The release liner 46 can be any release liner material known to those skilled in the art. Non-limiting examples of such release liners commercially available include siliconized polyethylene terephthalate films commercially available from H. P. Smith Co. and fluoropolymer coated polyester films commercially available from 3M under the brand "ScotchPak ™" release liners.

The therapeutic agent 48 can be any therapeutically active material known to those skilled in the art and approved for delivery topically to or transdermally or iontophoretically through the skin of a patient. Non-limiting examples of therapeutic agents useful in transdermal delivery devices are any active drug or salts of those.drUgs, used in topical or transdermal applications, or growth factors for use in enhancing wound healing. Other therapeutic agents identified as drugs or pharmacologically active agents are disclosed in U.S. Pat. Nos. 4,849,224 and 4,855,294, and PCT Patent Publication WO 89/07951.

Excipients or penetration enhancing agents are also known to those skilled in the art. Non-limiting examples of penetration enhancing agents include ethanol, methyl laurate, oleic acid, isopropyl myristate, and glycerol monolaurate. Other penetration enhancing agents known to those skilled in the art are disclosed in U.S. Pat. Nos. 4,849,224; and 4,855,294 and PCT Patent Publication WO 89/07951.

The method of manufacturing a transdermal delivery device depends on its construction.

The drug delivery device 40 shown in FIG. 4 can be prepared using the following general method. A solution is prepared by dissolving the therapeutic agent 48 and such optional excipients as are desired in a suitable solvent and mixed into either essentially unirradiated plasticizer prior to forming the composition, during the formation of the composition, or directly into the already formed composition. The resulting loaded adhesive composition is coated on the backing layer 42. A release liner 46 is applied to cover loaded adhesive layer 44.

A further description of the invention may be found in the following examples.

EXAMPLES

A number of examples of adhesive compositions of the present invention were prepared according to a process of the present invention. Approximately 100 grams of noncrosslinked poly(N-vinyl pyrrolidone) in a solid form of particles having a size of about 10 μm were placed in a resealable plastic bag and, except for comparative Example 8, were irradiated with ionizing radiation according to the irradiation type and dosage shown in Table I, followed by mixing of the resulting solid, radiation-crosslinked poly(N-vinyl pyrrolidone) homopolymer with a plasticizer of glycerin, water, or a mixture thereof. For irradiation by E-beam, an Energy Sciences Inc. Model CB-150 Electrocurtain Electron Beam Processor operating at a line speed of about 15 meters/minute and at 250 kV (except for Example 1 operating at 200 Kv) was used at ambient temperature and pressure. For radiation for Examples 9–12 using gamma radiation, an Atomic Energy of Canada, Inc. Model JS-7500 machine using a cobalt-60 high-energy source at ambient temperature and pressure.

Table I shows the resulting adhesive compositions and observations about the resulting adhesive composition.

TABLE I

| Example | N-vinyl Lactam Polymer | Type | Dosage (kGy) | Adhesive Composition (Wt. %) | Observation |
|---|---|---|---|---|---|
| 1 | nPVP | E-beam | 25** | 20% xPVP/80% H$_2$O | Slightly runny |
| 2 | nPVP | E-beam | 50 | 20% xPVp/80% H$_2$O | Thick, slightly adhesive |
| 3 | nPVP | E-beam | 75 | 20% xPVP/80% H$_2$O | Viscous, slightly adhesive |
| 4 | nPVP | E-beam | 100 | 33% xPVP/50% Gly/17% H$_2$O | Very tough adhesive |
| 5 | nPVP | E-beam | 100 | 33% xPVP/33.5% Gly/33.5% H$_2$O | Less strength, very adhesive |
| 6 | nPVP | E-beam | 100 | 33% xPVP/17% Gly/50% H$_2$O | Less viscous, good strength adhesive |
| 7 | nPVP | E-beam | 200 | 33% xPVP/18% Gly/49% H$_2$O | Very nice adhesive |
| 8* | nPVP | — | 0 | 33% xPVP/18% Gly/49% H$_2$O | Stringy gel |
| 9 | nPVP | Gamma | 75 | 30% xPVP/70% Gly | Firm, very pliable gel, very adhesive, slightly yellow, residues |
| 10 | nPVP | Gamma | 100 | 30% xPVP/70% Gly | Firm, very adhesive, pliable, slightly yellow, slight residue |
| 11 | nPVP | Gamma | 150 | 30% xPVP/70% Gly | Firm, pliable adhesive, slightly yellow, no residue |
| 12 | nPVP | Gamma | 200 | 30% xPVP/70% Gly | Firm, pliable adhesive, slightly yellow, no residue |

*Comparative Example
**200 kV, all other Examples 250 kV
nPVP - solid, non-crosslinked poly(N-vinyl pyrrolidone) homopolymer, from Aldrich Chemical (m.w. 360,000) for Example 1-8 and from BASF (K-90) for Examples 9-12
xPVP - solid, radiation-crosslinked poly(N-vinyl pyrrolidone) homopolymer
Gly - glycerin Examples 1–3 demonstrate the effect of irradiation dosage and its effect on the crosslinking of PVP. Increasing irradiation dosage increases the viscosity and cohesiveness of the adhesive composition, all other compositional parameters remaining constant.

Examples 4–6 demonstrate the differences in adhesive composition properties based on variation of the mixture of plasticizers. As the weight percentage of water increases, the viscosity and cohesivehess of the adhesive decreases, balanced by a decrease in adhesiveness.

Example 7 and Comparison Example 8 compare the effect of irradiation according to the process of the present invention. All other parameters being constant, the absence of irradiation of linear PVP fails to achieve adhesive properties required for the present invention. Further, a comparison of Example 7 with Example 6 shows acceptable adhesive properties within an irradiation dosage between 100 and 200 kGys (10–20 mrads).

Examples 9–12, differ from Examples 1–7 in that irradiation is provided by gamma high energy sources and the plasticizer is limited to glycerin. A comparison of Examples 9–12 shows decreasing presence of residue with increasing irradiation dosage balanced by a loss of some adhesiveness.

Example 13

100 grams of solid PVP (K-90 from BASF and of 10 μm particle size) were placed under nitrogen according to the following method. Samples, 100 grams each of solid PVP, were placed in 250 ml high density polyethylene bottle available from Nalgene and then place in a vacuum oven at ambient temperature. The vacuum oven was evacuated with a mechanical pump then filled with nitrogen until atmospheric pressure was obtained and this process was repeated 5 times for each sample at which time the bottle containing the samples was capped. While sealed in the nitrogen atmosphere, each sample was subjected to gamma irradiation of 150 kGys according to the procedures of Example 1.

Example 14

A container was charged with 75 grams of water, 16.25 grams of polyethylene glycol (MW 300) and 0.5 grams of KCl and mixed until dissolution. Then 8.5 grams of solid, crosslinked PVP prepared according to the method of Example 13,(K-90 from BASF, crosslinked with 150 kGys of gamma radiation) was added and the resultant composition was mixed in a blender until it was homogeneous. The adhesive composition was coated at five different thicknesses onto a 5.1 cm center strip of an 8.9 cm polyester backing, silver coated with E1700 silver ink from Ercon, Inc. of Waltham, Mass. The coated strips were dried in an oven at 65° C. for 15 minutes. One set of samples of five differing calipers, 2.54 cm×4.44 cm having an adhesive area of 2.54 cm×2.54 cm, was placed on each of six human panelists and adhesion to skin was measured as follows. Each sample was applied to the back of a human subject and rolled with a 2 kg roller to insure uniform application. Each sample was removed using a mechanical pulling device, consisting of a motor driven screw drive which pulls a 11.4 kg test line to which is attached a 2.54 cm wide metal clip. The metal clip is attached to each electrode sample at its 2.54 cm width during pulling testing. Electrodes were pulled in a plane parallel (180°) to the back at a rate of 13–14 cm/min. The adhesion data are reported in grams/2.54 cm and ranged from 24 grams/2.54 cm to 117 grams/2.54 cm. The caliper thicknesses varied from 0.25 mm to 1.27 mm wet and from 0.05 mm to 0.36 dry. The averages of results are shown in Table II.

TABLE II

| Example | Wet Caliper mm | Dry Caliper mm | Skin Adhesion g/2.54 cm |
|---|---|---|---|
| 14a | 0.25 | 0.050 | 24 |
| 14b | 0.51 | 0.127 | 47 |
| 14c | 0.76 | 0.178 | 62 |
| 14d | 1.02 | 0.254 | 87 |
| 14e | 1.27 | 0.356 | 117 |

Example 15

A non-release polyethylene terephthalate backing coated with silver ink (from Ercon, Inc., Waltham, Mass.) was coated at 0.76 mm with an adhesive composition of the present invention having 65 wt. percent water, 2 wt. percent potassium chloride and 35 wt. percent solid PVP (K-90 from BASF, crosslinked with 160 kGys gamma radiation). Electrodes were prepared to the dimensions of 2.54 cm×2.54 cm and then placed back to back. The following electrical data was measured for these electrodes on an Xtratek ET-65A ECG electrode tester from Xtratek of Lenexa, Kansas using Association for the Advancement of Medical Instrumentation (AAMI). approved procedures for measuring direct current offset and adhesive-adhesive impedance. D.C. offset was 2.2 mV and A.C. impedance was 26 ohms.

Example 16

To 50.0 grams of water was added 16.5 grams of plasticizer (PEG 300 from BASF) and 8.5 grams of solid PvP (crosslinked with 160 kGys of gamma radiation under a nitrogen atmosphere as described in Example 13). The mixture was stirred on a mixer for 10 minutes and then equilibrated for 24 hours. Then 13.29 grams of this mixture was loaded with 40 microliters of an ethanol solution containing 1 mCi Estradiol per milliliter of ethanol (Estradiol, tritium labeled, being obtained from NEN Research Products of Boston Mass.). The resulting suspension was then hand spread onto a polyethylene terephthalate substrate and then set in the hood open face to air dry for 1 week. One week later, 4 samples were prepared incorporating the air dried adhesive. Each sample was adhered to the stratum corneum side of a piece of excised mouse skin. Each of these samples were then placed into a Valia Chien glass diffusion cell (as described in "Drug Development and Industrial Pharmacy 1985 No. 11, p. 1195 which is incorporated by reference), such that the receiver cell was in contact with the subcutaneous tissue of the mouse skin. The area of exposed mouse skin was 0.67 $cm^2$. The temperature of the cell was 32° C. and the receiver cell solution was stirred at 600 rpm. The counts per minute (cpm) were measured at 17, 19, 22 and 24 hours using a Packard TRI-carb 460 CD Liquid Scintillation Counter. Four control samples were prepared to determine the cpm/mL of sample. Employing a density of 1.0 gram/mL for the dried adhesive, an average loading was determined to be $2.3 \times 16^6$ cpm/mL. The average permeability of Estradiol was then determined to be $4.6 \pm 0.6 \times 10^{-5}$ cm/hour with a lag time of 10 hours.

Example 17 and Comparative Example 18

Two samples of solid PVP (K-90 from BASF), one non-crosslinked and the other gamma irradiated at 150 kGys were extracted with acetone for 24 hours. The acetone-soluble extract of each sample was analyzed using a HP 5890 gas chromatograph from Hewlett Packard with an autosampler and a HP 3396 integrator from Hewlett Packard incorporating a 15 m DB-5 fused silica capillary, 0.25 mm ID, 0.25 micron film column. In both samples no detectable amount of N-vinyl-2-pyrrolidone was observed. Thus, irradiation of solid PVP did not produce detectable amounts of monomeric units. Crosslinking of solid PVP does not yield detectable amounts of fragments from commercially available PVP homopolymer.

Examples 19–32 and Comparative Examples 33–40

The following examples were used to discern the effect of various pre-conditions on solid PVP powders administered prior to gamma irradiation. Physical properties measured included Swelling Capacity S (mls of water absorbed/gm of PVP).

100 g samples of solid PVP (K-90 from BASF in a 10 μm size) were placed in 250 ml high density polyethylene bottles available from Nalgene. The samples were divided into 4 sets of pre-conditions.

No conditioning: used as received;

Pre-dry: samples dried overnight at 50° C. and 28 inches of Hg (711 Torr);

Purged: samples were placed in a vacuum oven at ambient temperature and the vacuum oven was evacuated with a mechanical pump, then filled with nitrogen until atmospheric pressure was obtained. This process was repeated three times prior to capping;

Pre-dry and Nitrogen Gas Purged: samples pre-dried as described in the second condition and nitrogen gas purged as described in the third condition.

Twelve samples covered the four pre-conditions and three gamma dose ranges: 125 kGys; 150 kGys; and 200 kGys were studied as Examples 19–30.

Example 31 differed from Example 25 in that K-90 flakes less than about 250 micrometers in size were used. Example 32 differed from Example 27 in that K-90 flakes less than about 250 micrometers in size were used. Comparative Example 33 was prepared using a chemical crosslinking agent diallyl maleate (DAM) according to the method disclosed in Example 2 of U.S. Pat. No. 4,931,282 (Asmus et al.), which is incorporated by reference herein, except that 0.08 parts DAM substituted for 0.16 parts of 3,3'-ethylene-bis-N-vinyl-2-pyrrolidone (EBVP). The particle size was less than about 300 micrometers in size., The PVP samples of Examples 19–32 and Comparative Example 33 were weighed into 20 ml glass vials. Distilled water was added to bring the mixture to 1% polymer solids. The samples were allowed 1 day to swell and were mixed with a spatula. Following another day, the samples were again mixed with a spatula and allowed to equilibrate for 2 weeks. The total height and gel height in the vial was measured in cm. Equation I above was used to calculate Swelling Capacity. Table III reports the results.

TABLE III

| Example | Gamma Dose (kGys) | Pre-Condition | PVP Weight gm | Water Weight gm | Total Height cm | Gel Height cm | Swelling Capacity S ml absorbed/gm polymer |
| --- | --- | --- | --- | --- | --- | --- | --- |
| 19 | 125 | None | .1546 | 15.33 | 33 | 25 | 75 |
| 20 | 125 | Pre-Dry | .1511 | 14.95 | 32 | 22.5 | 69 |
| 21 | 125 | N2 Purge | .1517 | 15.02 | 32 | 23 | 71 |
| 22 | 125 | Pre-Dry & N2 Purge | .1528 | 15.12 | 32.5 | 27 | 82 |
| 23 | 150 | None | .1515 | 15.01 | 32.5 | 22.5 | 68 |
| 24 | 150 | Pre-Dry | .1500 | 14.87 | 32 | 24.5 | 76 |
| 25 | 150 | N2 Purge | .1500 | 14.88 | 32 | 23 | 70 |
| 26 | 150 | Pre-Dry & N2 Purge | .1564 | 15.5 | 33 | 24 | 72 |
| 27 | 200 | None | .1570 | 15.57 | 33.5 | 24.5 | 73 |
| 28 | 200 | Pre-Dry | .1550 | 15.37 | 32 | 21.5 | 66 |
| 29 | 200 | N2 Purge | .1527 | 15.15 | 32.5 | 24 | 73 |
| 30 | 200 | Pre-Dry & N2 Purge | .1530 | 15.15 | 32 | 21.5 | 66 |
| 31 | 150 | N2 Purge | .1516 | 15.02 | 32 | 15 | 46 |
| 32 | 200 | None | .1522 | 15.02 | 32 | 14.5 | 44 |
| 33 | Chemically Crosslinked | None | .1533 | 15.20 | 32.5 | 15 | 45 |

In the Errede paper described above, the relationship between polymer swelling S in a given liquid is described as a function of the average number of backbone carbon atoms in polymer segments between crosslinked junctions, $\lambda$, according to Equation II above.

European. Patent Publication 0 322 098 (Duan) and U.S. Pat. No. 4,931,282 (Asmus et al.) identified useful chemical crosslinkers for crosslinking N-vinyl-2-pyrrolidone, in order to provide useful adhesive properties. One useful chemical crosslinking agent was EBVP. By plotting $\lambda^{\frac{1}{2}}$ vs S for the EBVP crosslinked system polymerized using method according to examples from U.S. Pat. No. 4,931,282, relative crosslinking of radiation processing according to the present invention to a conventional chemical approach can be compared.

Figure 5:
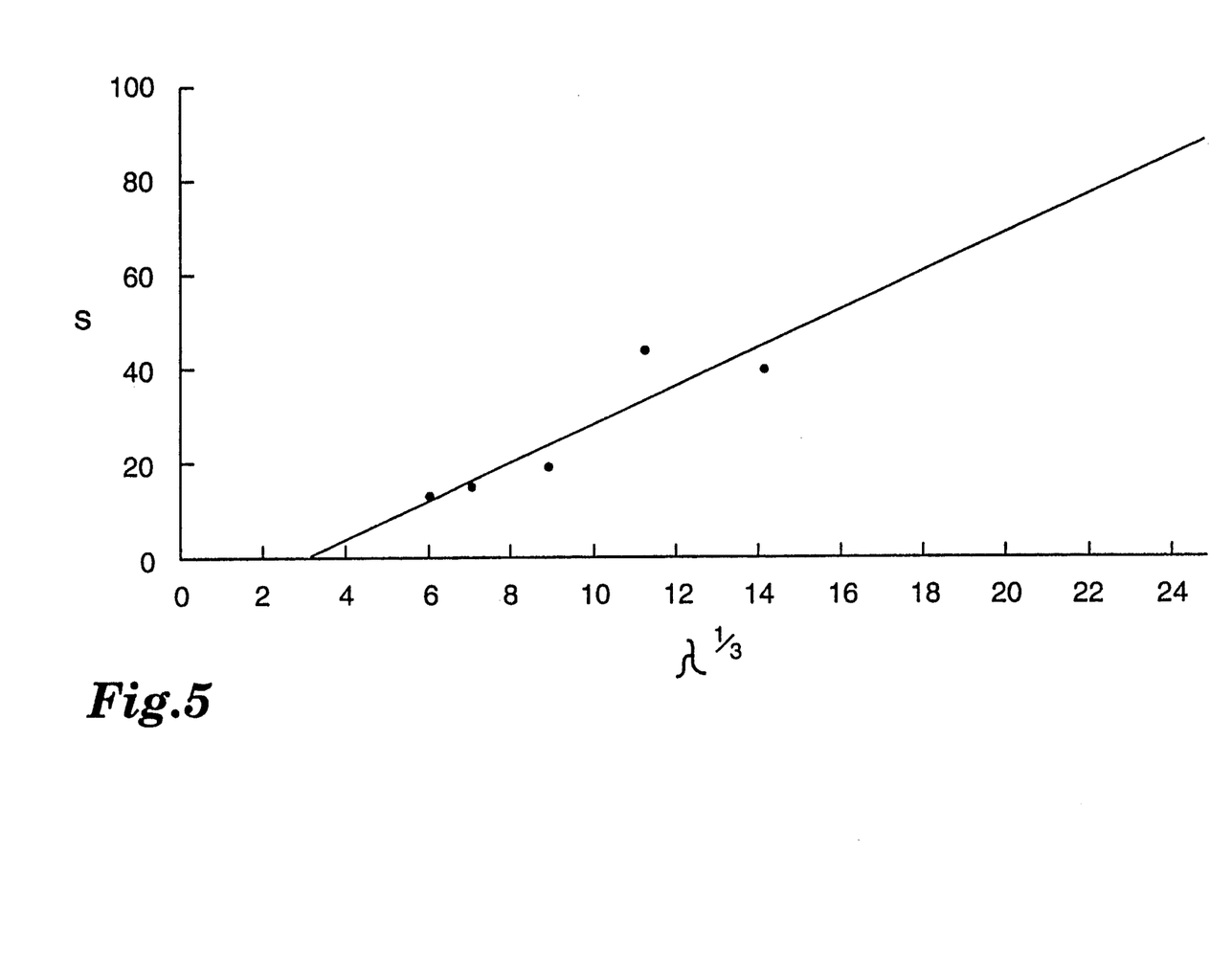
FIG. 5 is a graph comparing swelling capacity to the mole fraction of chemical crosslinker for comparative examples 34–40.

This comparison does not provide an absolute description of the crosslinked nature of the gamma irradiated polymer but rather provides an understanding that solid radiation-crosslinked PVP powders of the present invention act as though they are "very lightly" crosslinked. Table IV provides comparative EBVP data, measuring $1/\lambda$, which is crosslink density, and $\lambda^{\frac{1}{2}}$ to compute Swelling Capacity, S. FIG. 5 plots $\lambda^{\frac{1}{2}}$ and Swelling Capacity to provide additional analysis.

TABLE IV

| Comparative Example | U.S. Pat. No. 4,931,282 Example | Wt. Ratio EBVP/NVP | $1/\lambda$ | $\lambda^{\frac{1}{3}}$ | Swelling Capacity S* |
|---|---|---|---|---|---|
| 34 | 8 | 0.0002 | $8.95 * 10^{-5}$ | 22.36 | 10** |
| 35 | 13 | 0.0004 | $1.79 * 10^{-4}$ | 17.74 | 17** |
| 36 | 18 | 0.0008 | $3.58 * 10^{-4}$ | 14.08 | 0 |
| 37 | 23 | 0.0016 | $7.16 * 10^{-4}$ | 11.18 | 44 |
| 38 | 28 | 0.0032 | $1.43 * 10^{-3}$ | 8.88 | 19 |
| 39 | 33 | 0.0064 | $2.86 * 10^{-3}$ | 7.05 | 15 |
| 40 | 38 | 0.0128 | $5.69 * 10^{-3}$ | 6.00 | 13 |

*Determined according to method of Examples 19-33 above
**Considerable soluble fraction By comparison the S values of the swollen radiation-crosslinked PVP in Examples 19-32 ranged from 44-82 which according to correlation with data from Table IV and FIG. 5, compares to an EBVP crosslinked PVP gels having a $1/\lambda$ from about $5.7 * 10^{-3}$ to about $9 * 10^{-5}$. In fact EBVP crosslinked PVP gels under these bulk polymerization conditions do not form insoluble gels at the lower concentrations. See Comparative Examples 34 and 35. Thus, radiation crosslinking of solid PVP is a preferred method to provide a swellable PVP pressure-sensitive adhesive composition.

Examples 41-52 and Comparative Example 53

Radiation-crosslinked PVP powders prepared according to Examples 19-30 were formulated into the following adhesive composition of 4.0 grams of solid, radiation-crosslinked PVP; 0.25 grams of ethyl acetate used to reduce agglomeration of the powder during mixing with water; 9.3 grams of glycerol; and 66.45 grams of deionized water. The composition was coated on aluminum foil at a wet coating thickness of 0.38 mm, dried in an oven at 79° C. for 15 minutes and laminated to another strip of aluminum foil. T-peel adhesion tests according to ASTM method D1876 were determined on 2.54 cm wide samples drawn apart on an Instron tester with a Jaw Speed of 25.4 cm/min.

For comparison, DAM chemically crosslinked PVP was prepared according to the method of Example 2 of U.S. Pat. No. 4,931,282, except that 0.08 parts DAM substituted for 0.16 parts EBVP. A composition was prepared of 4.0 grams DAM crosslinked PVP; 0.25 grams of ethyl acetate; 9.3 grams of glycerol; and 66.45 grams of deionized water. The composition was tested by the same procedure for Examples 41-52, except that it had a wet coating thickness of 0.30 mm on aluminum foil.

The results are reported in Table V.

TABLE V

| Example | Gamma Dose | Pre-Condition | T-Peel Aluminum Foil (Average of 5 tests) (grams/2.54 cm) |
|---|---|---|---|
| 41 | 125 | None | 109 |
| 42 | 125 | Pre-Dry | 82 |
| 43 | 125 | N2 Purge | 95 |
| 44 | 125 | Pre-Dry & N2 Purge | 77 |
| 45 | 150 | None | 86 |
| 46 | 150 | Pre-Dry | 91 |
| 47 | 150 | N2 Purge | 97 |
| 48 | 150 | Pre-Dry & N2 Purge | 86 |
| 49 | 200 | None | 77 |
| 50 | 200 | Pre-Dry | 73 |
| 51 | 200 | N2 Purge | 77 |
| 52 | 200 | Pre-Dry & N2 Purge | 54 |
| 53 | X-linked with 0.08% DAM | None | 54 |

The results indicate that increased radiation dose reduces the gels' adhesive performance. The data also suggest that the combination of pre-drying and nitrogen gas purging increases the efficiency of crosslinking as is indicated by the lower adhesive performance at equivalent gamma dosage. All samples compare very favorably to. Comparative Example 53 of DAM crosslinked PVP by providing higher adhesion while maintaining cohesiveness.

Without being limited to the foregoing, the invention is hereby claimed.

What is claimed is:

1. A mammalian skin covering comprising: an adhesive layer for contacting mammalian skin and backing layer, the adhesive layer adhered to the backing layer and comprising a hydrophilic, pressure-sensitive adhesive composition of swellable, solid poly(N-vinyl lactam) radiation-crosslinked and an essentially unirradiated plasticizer present in an amount sufficient to form a cohesive, pressure-sensitive adhesive composition.

2. The mammalian skin covering according to claim 1, wherein the adhesive layer further comprises an antimicrobial agent.

3. The mammalian skin covering according to claim 1, wherein the backing layer comprises a film, substrate, or elastic, porous or breathable woven or nonwoven material.

4. The mammalian skin covering according to claim 1, further comprising a continuous pressure-sensitive adhesive matrix in which the pressure-sensitive adhesive composition is dispersed as discrete swollen gel particles in order to form a two phase composite adhesive layer.

5. The mammalian skin covering according to claim 1, wherein the covering comprises a medical tape, a wound dressing, a bandage or a medical skin covering.

6. A pharmaceutical delivery device comprising: an adhesive layer for contacting mammalian skin and a backing layer, the adhesive layer adhered to the backing layer and comprising a hydrophilic, pressure-sensitive adhesive composition of swellable, solid poly(N-vinyl lactam) radiation-crosslinked and an essentially unirradiated plasticizer present in an amount sufficient to form a cohesive, pressure-sensitive adhesive composition.

7. The pharmaceutical delivery device according to claim 6, wherein the adhesive layer further comprises a topical, transdermal, or iontophoretic therapeutic agent.

8. The pharmaceutical delivery device according to claim 7, wherein the adhesive layer further comprises an excipient, a solvent, or a penetration enhancing agent.

9. A hydrophilic, pressure-sensitive adhesive composition comprising: poly(N-vinyl lactam) radiation-crosslinked while in a solid form, an essentially unirradiated plasticizer present in an amount sufficient to form a cohesive, pressure-sensitive adhesive composition, and an anti-microbial agent.

10. The composition according to claim 9, wherein the amount of the essentially unirradiated plasticizer ranges from about 50 to about 90 weight percent of the composition.

11. The composition according to claim 9, wherein the amount of the essentially unirradiated plasticizer ranges from about 60 to about 80 weight percent of the composition.

12. The composition according to claim 9, wherein the poly(N-vinyl lactam) is poly(N-vinyl pyrrolidone) and the amount of the plasticizer ranges from about 60 to about 80 weight percent of the composition.

13. The composition according to claim 9, wherein the poly(N-vinyl lactam) is poly(N-vinyl-2-pyrrolidone) homopolymer.

14. The composition according to claim 9, wherein the poly(N-vinyl lactam) is a copolymer of N-vinyl-2-pyrrolidone monomer and a non-N-vinyl lactam comonomer selected from the group consisting of N,N-dimethylacrylamide, acrylic acid, methacrylic acid, hydroxyethylmethacrylate, acrylamide, vinyl acetate, and 2-acrylamido-2-methyl-l-propane sulfonic acid or its salt; the copolymer comprising N-vinyl-2-pyrrolidone monomeric units in an amount no less than about 50 weight percent of the poly(N-vinyl lactam).

15. The composition according to claim 14, wherein the copolymer comprises N-vinyl-2-pyrrolidone monomeric units in an amount from about 70 to about 100 weight percent of the poly(N-vinyl lactam).

16. The composition according to claim 9, wherein the radiation-crosslinked poly(N-vinyl lactam) has a Swelling Capacity of at least 15 milliliters of water per gram of the radiation-crosslinked poly(N-vinyl lactam).

17. The composition according to claim 9, wherein the plasticizer comprises a monohydric alcohol, a polyhydric alcohol, an ether alcohol, water, or combinations thereof.

18. The composition according to claim 17, wherein the plasticizer comprises water in an amount from about 20 to about 100 weight percent of the plasticizer.

19. A hydrophilic, pressure-sensitive adhesive composition comprising poly(N-vinyl lactam) radiation-crosslinked while in solid form, an essentially unirradiated plasticizer present in an amount sufficient to form a cohesive, pressure-sensitive adhesive composition, and a therapeutic agent.

20. The composition according to claim 19, wherein the amount of the essentially unirradiated plasticizer ranges from about 50 to about 90 weight percent of the composition.

21. The composition according to claim 19, wherein the amount of the essentially unirradiated plasticizer ranges from about 60 to about 80 weight percent of the composition.

22. The composition according to claim 19, wherein the poly(N-vinyl lactam) is poly(N-vinyl pyrrolidone) and the amount of the plasticizer ranges from about 60 to about 80 weight percent of the compos it ion.

23. The composition according to claim 19, wherein the poly(N-vinyl lactam) is poly(N-vinyl-2-pyrrolidone) homopolymer.

24. The composition according to claim 19, wherein the poly(N-vinyl lactam) is a copolymer of N-vinyl-2-pyrrolidone monomer and a non-N-vinyl lactam comonomer selected from the group consisting of N,N-dimethylacrylamide, acrylic acid, methacrylic acid, hydroxyethylmethacrylate, acrylamide, vinyl acetate, and 2-acrylamido-2-methyl-l-propane sulfonic acid or its salt; the copolymer comprising N-vinyl-2-pyrrolidone monomeric units in an amount no less than about 50 weight percent of the poly(N-vinyl lactam).

25. The composition according to claim 24, wherein the copolymer comprises N-vinyl-2-pyrrolidone monomeric units in an amount from about 70 to about 100 weight percent of the poly(N-vinyl lactam).

26. The composition according to claim 19, wherein the radiation-crosslinked poly(N-vinyl lactam) has a Swelling Capacity of at least 15 milliliters of water per gram of the radiation-crosslinked poly(N-vinyl lactam)

27. The composition according to claim 19, wherein the plasticizer comprises a monohydric alcohol, a polyhydric alcohol, an ether alcohol, water, or combinations thereof.

28. The composition according to claim 27, wherein the plasticizer comprises water in an amount from about 20 to about 100 weight percent of the plasticizer.

* * * * *

UNITED STATES PATENT AND TRADEMARK OFFICE
CERTIFICATE OF CORRECTION

PATENT NO. : 5,389,376
DATED : February 14, 1995
INVENTOR(S) : Duan et al

It is certified that error appears in the above-indentified patent and that said Letters Patent is hereby corrected as shown below:

On the title page: Item [75] should be deleted.

Column 22, line 8 and 9, "compos it ion" should read --composition --.

Signed and Sealed this

Nineteenth Day of December, 1995

Attest:

BRUCE LEHMAN

Attesting Officer

Commissioner of Patents and Trademarks